(12) United States Patent
Leggett, Jr. et al.

(10) Patent No.: US 12,234,517 B2
(45) Date of Patent: Feb. 25, 2025

(54) METHOD OF EVALUATING PRE-CANCEROUS OR CANCEROUS LESIONS FOR ORAL CANCER

(71) Applicant: THOMAS K. LEGGETT, LLC, Cairo, GA (US)

(72) Inventors: Thomas K. Leggett, Jr., Whigham, GA (US); Rachel Edin Leggett, Whigham, GA (US); Carol G. Leggett, Whigham, GA (US)

(73) Assignee: THOMAS K. LEGGETT, LLC, Cairo, GA (US)

( * ) Notice: Subject to any disclaimer, the term of this patent is extended or adjusted under 35 U.S.C. 154(b) by 0 days.

(21) Appl. No.: 17/446,995

(22) Filed: Sep. 7, 2021

(65) Prior Publication Data

US 2022/0098675 A1    Mar. 31, 2022

Related U.S. Application Data

(60) Provisional application No. 63/085,213, filed on Sep. 30, 2020.

(51) Int. Cl.
  *C12Q 1/6886* (2018.01)
(52) U.S. Cl.
  CPC ..... *C12Q 1/6886* (2013.01); *C12Q 2600/156* (2013.01)
(58) Field of Classification Search
  None
  See application file for complete search history.

(56) References Cited

U.S. PATENT DOCUMENTS 10,023,919 B2    7/2018   Maitra et al.

FOREIGN PATENT DOCUMENTS

WO    WO-2010115442 A1 * 10/2010 ............... A23G 4/06

OTHER PUBLICATIONS

Eychner et al. Assessing DNA recovery from chewing gum. Med Sci Law. Jan. 2017;57(1):7-11. doi: 10.1177/0025802416676413. Epub Oct. 28, 2016. PMID: 27794077 (Year: 2017).*
Vega et al. p53 exon 5 mutations as a prognostic indicator of shortened survival in non-small-cell lung cancer. British journal of cancer.(1997). 76. 44-51. 10.1038/bjc.1997.334.; (Year: 1997).*

(Continued)

*Primary Examiner* — Aaron A Priest
*Assistant Examiner* — Tian Yu
(74) *Attorney, Agent, or Firm* — ALLEN, DYER, DOPPELT + GILCHRIST, PA

(57) ABSTRACT

A method of collecting oral mucosal cells from a patient and evaluating the oral mucosal cells for oral squamous cell carcinoma predisposition in the patient includes collecting a sample of chewing gum from a patient that had chewed the chewing gum for a minimum of about 5 minutes up to about 30 minutes. The chewing gum includes a molecular adherent targeted towards oral mucosal cells with oral squamous cell carcinoma predisposition. A polymerase chain reaction (PCR) is performed on a DNA template prepared from the chewed chewing gum using oligonucleotide primers that are selected to amplify nucleic acids that screen for genomic sequence variations seen in genes that are indicative of oral squamous cell carcinoma predisposition in the patient.

5 Claims, 6 Drawing Sheets

Specification includes a Sequence Listing.

(56) References Cited

OTHER PUBLICATIONS

Addgene: Protocol—How to Run an Agarose Gel; Published Feb. 2018; accessed online Jan. 4, 2024 (Year: 2018).*
'Chewing Gum.' Wikipedia, last modified Sep. 2019; Accessed on Jan. 10, 2024 (Year: 2019).*
Klaahsen, D. Avoiding false positives with PCR: IDT. Integrated DNA Technologies.; Published 2013, Apr. 27; www.idtdna.com (Year: 2013).*
Kramer, Martha F., and Donald M. Coen. "Enzymatic amplification of DNA by PCR: standard procedures and optimization." Current protocols in cell biology 10.1 (2001): A-3F. (Year: 2001).*
Mikhailov, Oleg V. "Molecular structure design and soft template synthesis of aza-, oxaaza-and thiaazamacrocyclic metal chelates in the gelatin matrix." Arabian journal of Chemistry 10.1 (2017): 47-67. (Year: 2017).*
Yang et al., The Expression and Correlation of iNOS and p53 in Oral Squamous Cell Carcinoma. Biomed Res Int. 2015;2015: 637853. doi: 10.1155/2015/637853. Epub Oct. 7, 2015. PMID: 26523280; PMCID: PMC4615849 (Year: 2015).*
Guvendiren et al. (2012). 9.22—Photopolymerizable Systems. In Polymer Science: a Comprehensive Reference: vol. 1-10 (pp. 413-438). Elsevier (Year: 2012).*
Kramer et al. "Enzymatic amplification of DNA by PCR: standard procedures and optimization." Current protocols in cell biology 10.1 (2001): A-3F (Year: 2001).*
Klaahsen, D. Avoiding false positives with PCR: IDT. Integrated DNA Technologies.; Published Apr. 27, 2013; www.idtdna.com (Year: 2013).*
Eychner et al. Assessing DNA recovery from chewing gum. Med Sci Law. Jan. 2017;57(1):7-11. doi: 10.1177/0025802416676413. Epub Oct. 28, 2016. PMID: 27794077; cited as NPL document #1, on IDS filed Sep. 7, 2021 (Year: 2017).*
Vega et al. p53 exon 5 mutations as a prognostic indicator of shortened survival in non-small-cell lung cancer. British journal of cancer.(1997). 76. 44-51. 10.1038/bjc.1997.334.; cited as NPL document #3, on IDS filed Sep. 7, 2021 (Year: 1997).*
Wikipedia—Agarose gel electrophoresis ('Agarose gel electrophoresis.' Wikipedia, Archived on Aug. 22, 2018 on WaybackMachine ) (Year: 2018).*
Eychner et al., "Assessing DNA Recovery From Chewing Gum," Medicine, Science and the Law; vol. 57(1); Jan. 2017; pp. 7-11.
Sabarinathan et al., "Production of Polyhydroxybutyrate (PHB) from Pseudomonas Plecoglossicida and Its Application Towards Cancer Detection," Informatics in Medicine Unlocked 11; 2018; pp. 61-67.
Vega et al., "p53 Exon 5 Mutations as a Prognostic Indicator of Shortened Survival in Non-Small-Cell Lung Cancer," British Journal of Cancer; 76(1); 1997; pp. 44-51.
Asgharzadeh et al., "Prognostic Significance of Gene Expression Profiles of Metastatic Neuroblastomas Lacking MYCN Gene Amplification," Journal of the National Cancer Institute; vol. 98, No. 17; Sep. 6, 2006, pp. 1193-1203.
Kuba et al., "The Impact of MYC Amplification on Clinicopathologic Features and Prognosis of Radiation-Associated Angiosarcomas of the Breast," Histopathology; 79(5); Nov. 2021; pp. 836-846.
Jansen et al., "FGF-2-Loaded Collagen Scaffolds Attract Cells and Blood Vessels in Rat Oral Mucosa," Journal of Oral Pathology & Medicine (2009) 38: pp. 630-638.
Sakurai et al., "Clinical Significance of Integrin αV and β Superfamily Members and Focal Adhesion Kinase Activity in Oral Squamous Cell Carcinoma: A Retrospective Observational Study," Pathology & Oncology Research; Published by Frontiers; Jan. 18, 2024; pp. 1-11.
Elango et al., "The Molecular Interaction of Collagen with Cell Receptors for Biological Function," Polymers 2022, 14, 876; Feb. 23, 2022; pp. 1-25.
Larjava et al., "Epithelial Integrins with Special Reference to Oral Epithelia," Critical Reviews in Oral Biology & Medicine; Journal of Dental Research 90(12); Feb. 7, 2011; pp. 1367-1376.
Aedma et al., "Li-Fraumeni Syndrome," National Library of Medicine, National Institutes of Health; StatPearls Publishing; Jan. 2024; pp. 1-17.
Deekshit et al., "Mismatch Amplification Mutation Assay-Polymerase Chain Reaction: A Method of Detecting Fluoroquinolone Resistance Mechanism in Bacterial Pathogens," Indian Journal of Medical Research 149(2); Feb. 2019; pp. 146-150.
Waasdorp et al., "The Bigger Picture: Why Oral Mucosa Heals Better Than Skin," Biomolecules, 2021, 11, 1165; Aug. 6, 2021; pp. 1-22.
Kim et al., "Absence of Amplification of HER-2/neu (c-erbB-2) Gene in Ewing's Sarcoma: A Real-Time Polymerase Chain Reaction Method," Pathology Research and Practice; vol. 200, 10; Dec. 2004; pp. 663-667.
Wang et al., "Gelatin-Based Hydrogels for Organ 3D Bioprinting," Polymers 9, 401; Aug. 30, 2017; pp. 1-24.

* cited by examiner

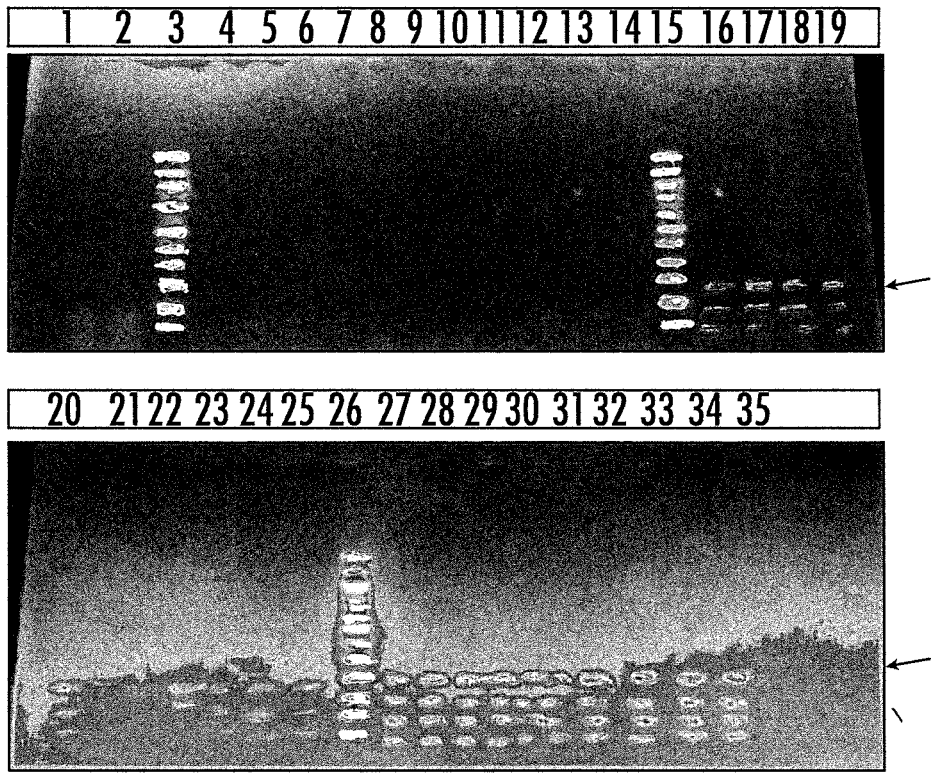

ARROWS POINTING AT JUST UNDER 200 BP (100 BP LADDER) REPRESENT POSITION OF EXPECTED AMPLICON
LANES 3, 15, 26 CONTAINED 100 BP LADDER FROM NEW ENGLAND BIOLABS #N0551S
LANES 4-13 PRIMER 5 FROM EXON 5 OF THE TP53 GENE - NO AMPLIFIED PRODUCT
LANES 16-25 PRIMER 7 FROM EXON 7 OF THE TP53 GENE - INCONCLUSIVE RESULTS (ALL BUT 1 SAMPLE AMPLIFIED)
LANES 28-35 PRIMER 8 FROM EXON 8 OF THE TP53 GENE - AMPLICON PRODUCED, DIFFERENTIAL SAMPLE AMPLIFICATION

FIG. 5

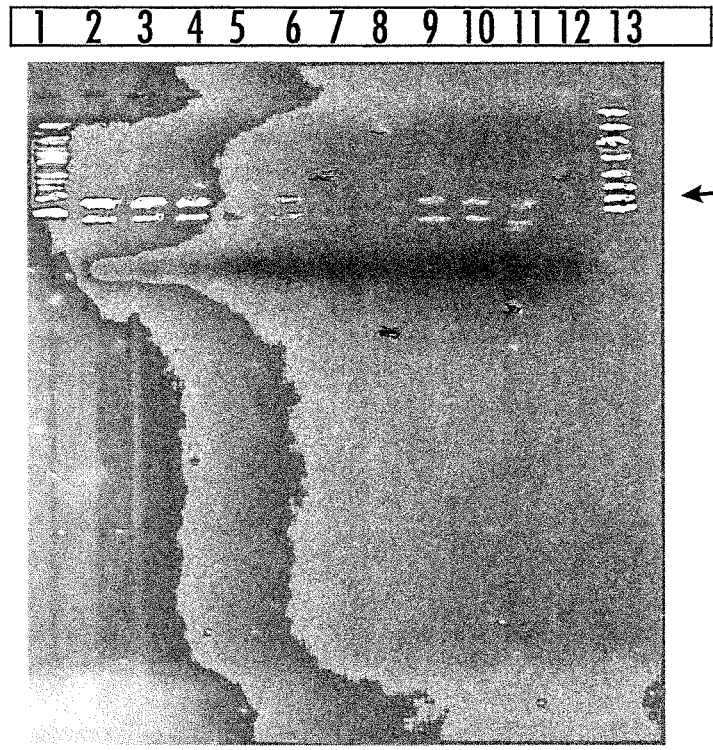

ARROW INDICATES EXPECTED AMPLICON LOCATION OF SLIGHTLY LESS THAN 200 BP

LANES 1 AND 13 - 100 BP LADDER FROM NEW ENGLAND BIOLABS
LANE 2 - NON-SMOKER GUM WITH COLLAGEN - AMPLICON
LANE 3 - NON-SMOKER GUM WITH COLLAGEN - AMPLICON
LANE 4 - NON-SMOKER GUM WITH COLLAGEN - AMPLICON
LANE 5 - PAST SMOKER GUM WITH KAOLIN - NO AMPLICON
LANE 6 - NON-SMOKER GUM NO ADDITIVE (SAME INDIVIDUAL AS LANE 2; FLUORESCENT SIGNAL NOT AS INTENSE)
LANE 7 - PAST SMOKER NO ADDITIVE - NO AMPLICON
LANE 8 - ORAL CANCER PATIENT - NO ADDITIVE - NO AMPLICON
LANE 9 - ORAL CANCER PATIENT - COLLAGEN - SLIGHT AMPLIFICATION
LANE 10 - ORAL CANCER PATIENT - WITH KAOLIN - SLIGHT AMPLIFICATION
LANE 11 - ORAL CANCER PATIENT - WITH KAOLIN - SLIGHT AMPLIFICATION
LANE 12 - NEGATIVE CONTROL - ONLY WATER

FIG. 6

SEQUENCE LISTING

```
<160> NUMBER OF SEQ ID NOS: 6

<210> SEQ ID NO 1
<211> LENGTH: 21
<212> TYPE: DNA
<213> ORGANISM: Homo sapiens

<400> SEQUENCE: 1
tttcaactct gtctccttcc t                                              21

<210> SEQ ID NO 2
<211> LENGTH: 19
<212> TYPE: DNA
<213> ORGANISM: Homo sapiens

<400> SEQUENCE: 2
gccccagctg ctcaccatc                                                 19

<210> SEQ ID NO 3
<211> LENGTH: 20
<212> TYPE: DNA
<213> ORGANISM: Homo sapiens

<400> SEQUENCE: 3
gtgttgtctc ctaggttggc                                                20

<210> SEQ ID NO 4
<211> LENGTH: 20
<212> TYPE: DNA
<213> ORGANISM: Homo sapiens

<400> SEQUENCE: 4
tgtgcagggt ggcaagtggc                                                20

<210> SEQ ID NO 5
<211> LENGTH: 20
<212> TYPE: DNA
<213> ORGANISM: Homo sapiens

<400> SEQUENCE: 5
cctatcctga gtagtggtaa                                                20

<210> SEQ ID NO 6
<211> LENGTH: 21
<212> TYPE: DNA
<213> ORGANISM: Homo sapiens

<400> SEQUENCE: 6
tcctgcttgc ttacctcgct t                                              21
```

METHOD OF EVALUATING PRE-CANCEROUS OR CANCEROUS LESIONS FOR ORAL CANCER

PRIORITY APPLICATION

This application is based upon provisional application Ser. No. 63/085,213, filed Sep. 30, 2020, the disclosure which is hereby incorporated by reference in its entirety.

REFERENCE TO AN ELECTRONIC SEQUENCE LISTING

The contents of the electronic sequence listing (Leggett ST25.txt; size: 1,152 bytes; and Date of Creation: Nov. 5, 2023) is herein incorporated by reference in its entirety.

FIELD OF THE INVENTION

This invention relates to evaluating pre-cancerous or cancerous lesions for oral cancer, and more particularly, to a method for collecting oral mucosal cells from a patient and evaluating for pre-cancerous or cancerous lesions.

BACKGROUND OF THE INVENTION

The first cancer screening method was developed in 1923 by George Papanicolaou. Despite its potential, it was received with skepticism in the medical community and did not become the widely used "pap smear," as it is currently known, until the American Cancer Society promoted it during the early 1960's. Now, an entire century later, there is still no routine screening test for oral cavity cancers. An asymptomatic individual must rely entirely on the naked eye of their dental provider and often, neoplasms go undetected until they have grown or metastasized to other tissues.

Oral DNA has been assessed by recovering the DNA from chewing gum, such as used for forensic evidence. For example, the article by Eychner et al. entitled, "Assessing DNA Recovery From Chewing Gum," Medicine, Science in the Law, 2017, Volume 57(1); 7-11, describes a process for evaluating DNA extraction methods to yield the highest quantity of DNA from chewing gum. Different extraction techniques were tested and the quantity of DNA recovered from chewing gum was determined using real-time polymerase chain reaction (PCR) with a Quantifiler™ human DNA quantification kit. Chewed gum control samples from healthy adult donors were compared with discarded environmental chewing gum samples simulating forensic evidence. The different methods all yielded sufficient amplifiable human DNA from chewing gum using a wet-swab technique. In one example, the control would chew gum for at least 30 minutes. A spin column was used as a separation device.

A technique for extracting DNA from chewing gum is also taught in U.S. Pat. No. 10,023,919, which discloses the use of sonication and amplifying the nucleic acid extracted from a microorganism or cell, such as using PCR. The gum may be chewed for up to 10 minutes followed by sonication and then using PCR for bacterial DNA analysis. The technique is particularly applicable for detecting and quantitating microorganisms that adhere to the chewing gum, followed by analyzing the DNA from the bacteria that could be present in the oral cavity of a patient. In a specific aspect disclosed in the '919 patent, the method extracts nucleic acids from a polymer, such a chewing gum, that is malleable within a living organism. The polymer is contacted with chloroform and a buffer solution. The chloroform is separated from the buffer solution. The nucleic acids are extracted from the polymer contained within the buffer. The nucleic acids are amplified using at least one oligonucleotide primer specific for the microorganism, such as using the well-known polymerase chain reaction (PCR). The absence of nucleic acids in the buffer solution is indicative of a polymer that is resistant to the attachment of the microorganism.

Techniques are desired that are more specific to evaluating pre-cancerous or cancerous lesions for oral cancer in a patient such as better techniques for determining the extent of OSCC (Oral Squamous Cell Carcinoma) indicative of possible head and throat cancer.

SUMMARY OF THE INVENTION

In general, a method of collecting oral mucosal cells from a patient and evaluating the oral mucosal cells for oral squamous cell carcinoma predisposition in the patient may comprise collecting a sample of chewing gum from a patient that had chewed the chewing gum for a minimum of about 5 minutes up to about 30 minutes. The chewing gum may include a molecular adherent targeted towards oral mucosal cells with oral squamous cell carcinoma predisposition. The method includes performing a polymerase chain reaction (PCR) on a DNA template prepared from the chewed chewing gum using oligonucleotide primers that are selected to amplify nucleic acids that screen for genomic sequence variations seen in genes that are indicative of oral squamous cell carcinoma predisposition in the patient.

In an example, the molecular adherent may comprise collagen and may comprise a gum base having about 1% to about 4% of added collagen. The molecular adherent may comprise Polyhydroxyalkanotate or a copolymer thereof. The oligonucleotide primers may be selected for PCR to screen for genomic sequence variations located on exon 8 of the TP53 gene located in chromosome 17 of the patient. An oligonucleotide primer sequence for a forward primer may be (SEQ ID NO: 5): CCT ATC CTG AGT AGT GGT AA, the sequence for a reverse primer is (SEQ ID NO: 6): TTC TGC TTG CTT ACC TCG CTT. An amplicon length for the DNA template may be about 165 base pairs. The DNA template may be prepared by physically chopping, sonicating, vortexing or exposing the chewing gum to electromagnetic radiation.

The method may also include collecting messenger RNA (mRNA) from the collected sample of chewing gum, applying reverse transcriptase to produce complementary DNA (cDNA), and enumerating expression levels of pre-cancerous or cancerous genetic mutations indicative of oral squamous cell carcinoma predisposition in the patient. The method may include separating cellular proteins from the collected sample of chewing gum using sodium dodecyl sulfate-polyacrylamide gel electrophoresis (SDS-PAGE) gel that is transferred to a solid-phase material followed by Western blotting to determine the presence of protein that indicates a pre-cancerous or cancerous mutation in a gene indicative of oral squamous cell carcinoma predisposition in the patient. The method may include loading a liquid containing the DNA template after PCR amplification onto an agarose gel containing an ethidium bromide solution in a Tris-Acetate buffer and running the gel for about 75 minutes at about 80 volts.

DESCRIPTION OF THE DRAWINGS

Other objects, features and advantages of the present invention will become apparent from the detailed description of the invention, which follows when considered in light of the accompanying drawings in which:

FIG. 5 shows gel electrophoresis results showing primer set efficiency.

FIG. 6 shows gel electrophoresis results showing the efficiency of a primer detecting mutations within the priming sites of exon 8 in the TP53 gene.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Figure 1:
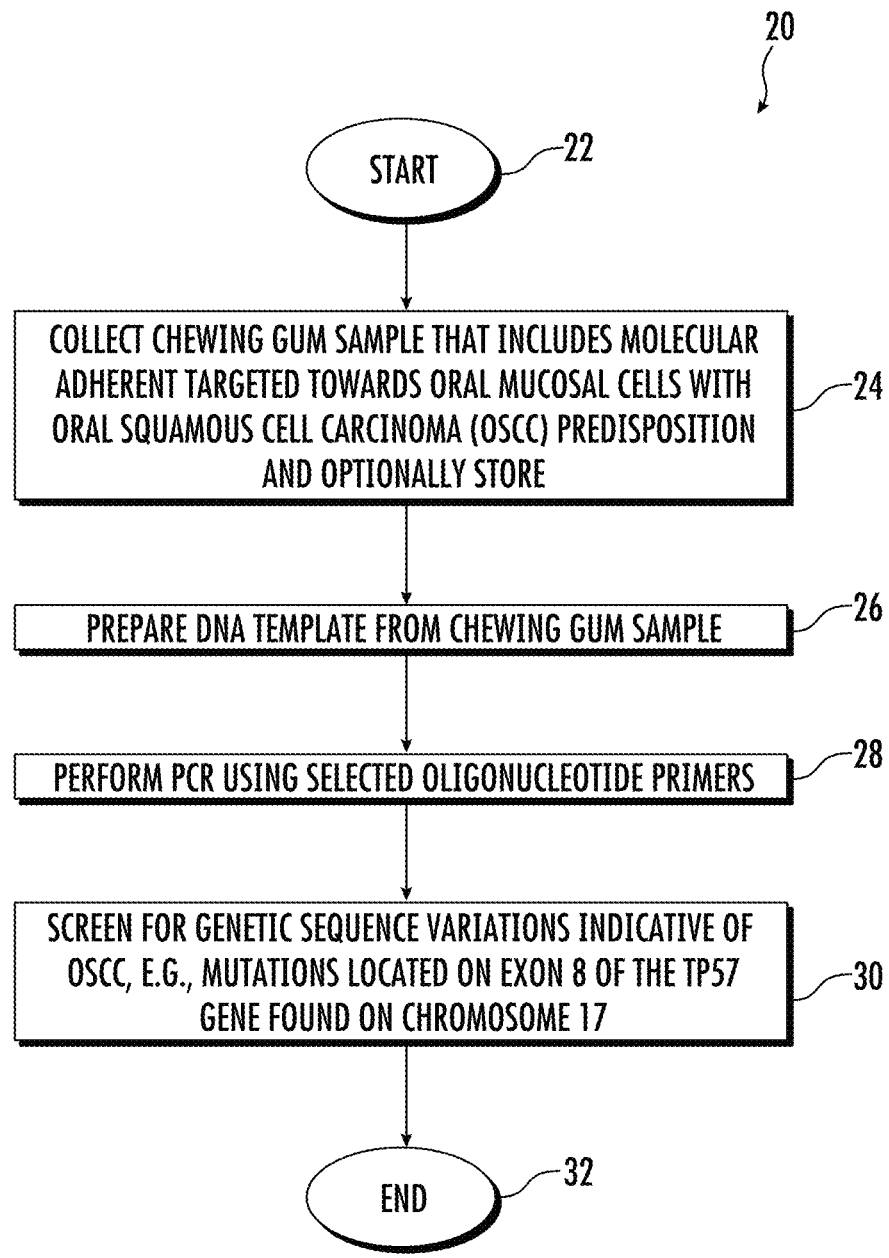
FIG. 1 is a high-level flowchart of an example method of collecting oral mucosal cells from a patient and evaluating the oral mucosal cells for oral squamous cell carcinoma (OSCC) in the patient in accordance with a non-limiting example.

A flowchart of an example high level process is shown generally at 20 in FIG. 1. The process starts (Block 22) and a sample of chewing gum is collected from a patient that had chewed the chewing gum for a minimum of about 5 minutes up to about 30 minutes. The chewing gum includes a molecular adherent targeted towards oral mucosal cells with oral squamous cell carcinoma predisposition (Block 24). The chewing gum sample may be optionally stored and frozen for later analysis or processed on location. A DNA template is prepared from the chewing gum sample (Block 26) and a polymerase chain reaction (PCR) is performed on a DNA template prepared from the chewed chewing gum using oligonucleotide primers that are selected to amplify nucleic acids that screen for genomic sequence variations seen in genes that are indicative of oral squamous cell carcinoma predisposition in the patient (Block 28). Screening for genetic sequence variations may be indicative of OSCC and, for example, may be mutations located on exon 8 of the TP57 gene found on chromosome 17 (Block 30). The process ends (Block 32).

As noted before, the molecular adherent may be formed from collagen and the chewing gum may be formed as a gum base having about 1% to about 4% of added collagen. In another aspect, the molecular adherent may be formed from Polyhydroxyalkanotate (PHA) and preferably a short-chain PHA such as polyhydroxybutyrate (PHB) or a copolymer of PHB such as PHBV or PHBH. The shorter chain polymers are more crystalline and hard and found to be more attractive to certain proteins such as oral mucosal cells that have the OSCC predisposition. The DNA template may be prepared by physically chopping, sonicating, vortexing, or exposing the chewing gum to electromagnetic radiation.

Reference is also made to the article by Vega et al. entitled, "p53 Exon 5 Mutations as a Prognostic Indicator of Shortened Survival in Non-Small-Cell Lung Cancer," British Journal of Cancer (1997), which article is incorporated by reference in its entirety. This article concluded the location of p53 mutations may be considered a prognostic indicator for the evaluation of poor evaluation in non-small-cell lung cancer patients.

Figure 2:
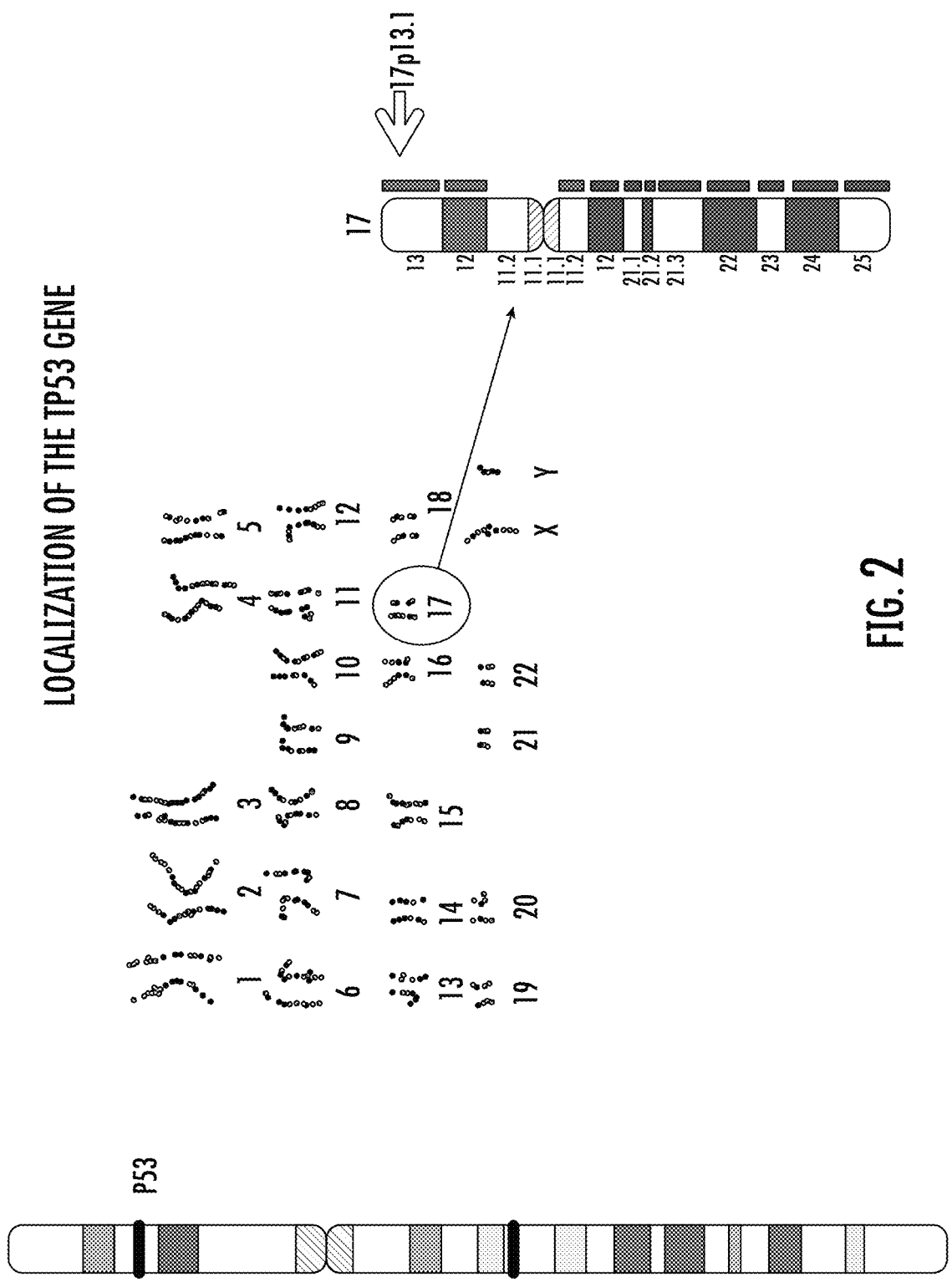
FIG. 2 is a diagram showing the localization of the Tumor Protein P53 (TP53) gene on chromosome 17.
Figure 3:
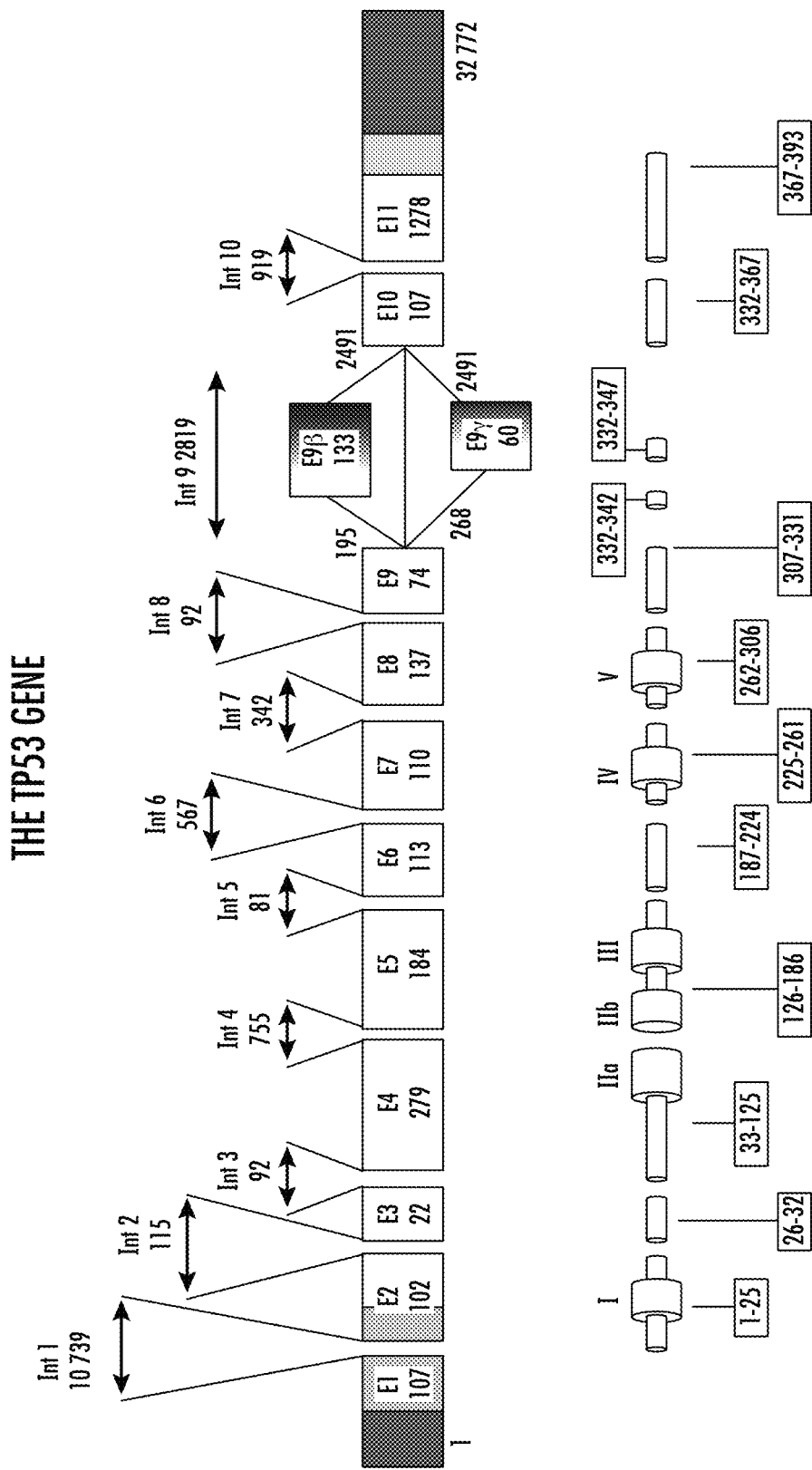
FIG. 3 is a diagram showing details of the TP53 gene.

An experiment tested the strength of a collagen-enriched chewing gum against a normal chewing gum control for diagnostic potential of those with predisposing oral cancer markers. The objective of the experiment was to determine the benefit of enriching chewing gum with a molecular adherent targeted towards cells with oral squamous cell carcinoma predisposition. By making normal chewing gum and adding collagen peptides, in this example, it was possible to increase attachment of oral mucosal cells to accumulate enough preneoplastic cells to verify diagnostic potential. Upon collection of the sample, polymerase chain reaction was completed to screen for a mutation located on exon 8 of the TP53 gene found on chromosome 17. An example of a diagram showing the localization of the TP53 gene on chromosome 17 (circled) is shown in FIG. 2, and a diagram showing details of the TP53 gene is shown in FIG. 3. The chromosome 17 p 13.1 (P53 locus) is shown in FIG. 2. It is possible that the p53 protein and p53-immunopositive lesions may show p53 mutations and be found in a large percentage of tumors, and the conducted experiments showed that primers may be selected to screen for genomic sequence variations located on exon 8 of the TP53 gene.

The gum base used in this experiment was made from a do-it-yourself bubble gum kit (Product code 5540000002) by Copernicus Toys. The collagen additive was obtained as multi-collagen peptides (Product code XOO2D0LHCV) from Health Revolution. The gum was prepared according to the package directions. The control gum contained 24.79 grams of gum base into which 6.97 grams of powdered sugar was incorporated. The collagen gum was prepared with 37.8 grams of gum base into which was incorporated 9.44 grams of a mixture of 12.98 grams of powdered sugar and 0.515 grams of collagen. In an example, the collagen may be about 1-4% by weight of the total chewing gum sample to be given to a patient for chewing. Other ranges may be determined.

The chewing gum was divided into pieces weighing between 5-6 grams, wrapped in parchment paper and placed in a −20° C. freezer. The chewing gum was given to nine individuals. One of the individuals had been diagnosed by tissue biopsy to have invasive squamous cell carcinoma, one of the individuals was a smoker, two of the individuals had a history of smoking with cessation, one individual was a user of smoke-less tobacco, and two individuals had no history of tobacco use. The participants were instructed to chew the chewing gum for ten minutes then wrap it back in the parchment paper. The gum was kept in a −20° C. freezer until analysis. Although the participants chewed the chewing gum for about 10 minutes, adequate results should be obtainable when the chewing gum is chewed for about 5 minutes to about 30 minutes. Enough time should be given for the gum with the added molecular adherent, such as collagen, to pick up and retain the necessary cells for analysis.

The DNA template for the polymerase chain reaction was prepared by placing 105 milligrams (+/−4 mg) of the chewed chewing gum into a sterile two milliliter Eppendorf® tube containing 250 microliters of sterile saline. The gum mixture was vortexed, and the liquid was used as template in the polymerase chain reaction.

Oligonucleotide primers were ordered from Integrated DNA Technologies for specific sequences in exon 8 of the p53 gene. The sequence for the forward primer was (SEQ ID NO: 5): CCT ATC CTG AGT AGT GGT AA. The sequence for the reverse primer was (SEQ ID NO: 6): TCC TGC TTG CTT ACC TCG CTT. The amplicon length was 165 base pairs in this example. The polymerase chain reaction was performed in a BioMetra thermal cycler using 10 microliters of Promega 2X Go Taq™ Green Master Mix, 2 microliters (0.1 nanomole per microliter) each of the forward and reverse primers (10 nm), and 6 microliters of the template solution. The PCR was run for 35 cycles at 55° C. annealing, 72° C. extension, and 4° C. hold.

Following amplification, the 15 microliters of sample was loaded onto a 1.8% agarose gel containing 0.0001% of an ethidium bromide solution. Tris Acetate EDTA (TAE) buffer from Fisher BioReagents (BP 13354) was used as the running buffer. A DNA Quick Load 100 base pair ladder obtained from New England Biolabs was used as a marker. The electrophoresis gel was run for approximately 75 minutes at 80 volts. The agarose gel was placed on a Major Science UV transilluminator and the bands were photographed at 365 nanometers.

Four experiments were completed via PCR. Experiments 1 and 2 were run to determine the diagnostic potential of three different exons located on the TP53 gene of chromosome 17. After concluding that exon 8 yielded the highest indicative capability, three more experiments were run to compare the collagen-enriched chewing gum against the control chewing gum. Experiments 3 and 4 revealed that exon 8 is an indicator of mutations in the specific 163 base pairs of the TP53 gene utilized and provided insight on the presence of the mutation in smokers vs non-smokers. Experiment 2 provided evidence of the optimal annealing temperature and cycle number for amplification of the mutation found in exon 8.

Figure 4:
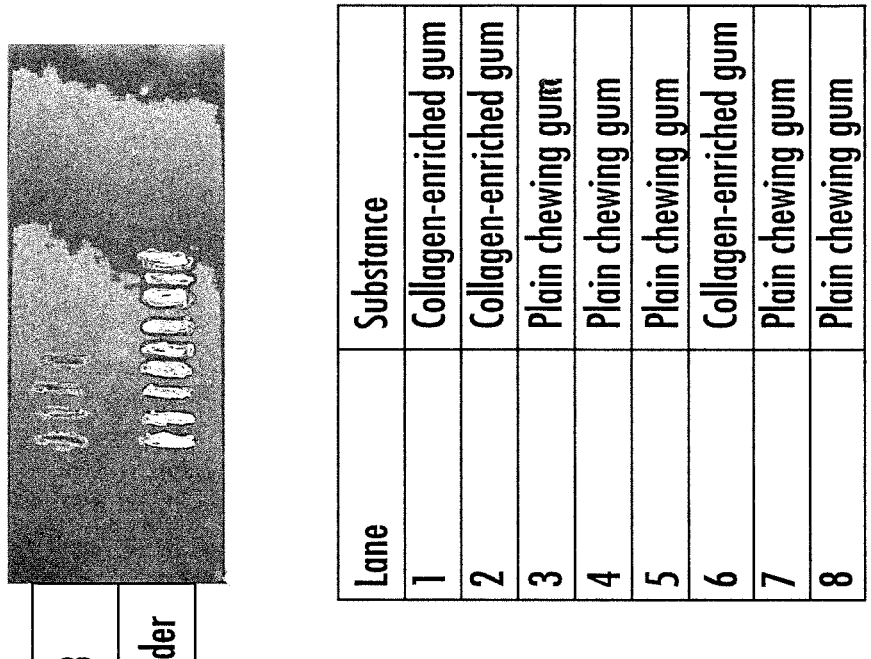
FIG. 4 shows gel electrophoresis results from experiment 2 regarding exon 8 and the accompanying chart identifying each lane/ladder as either collagen-enriched chewing gum or plain chewing gum.
Figure 4:
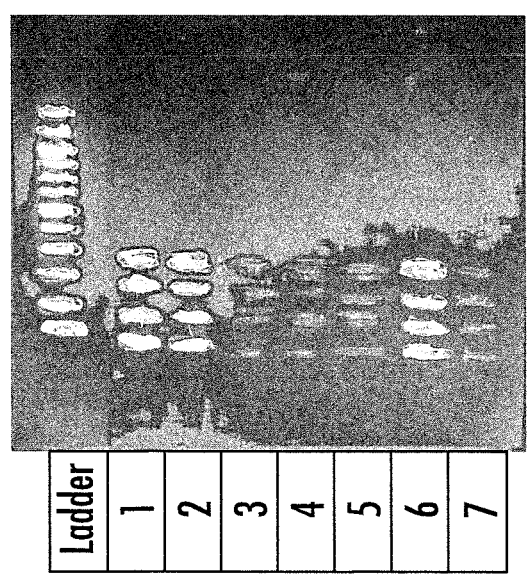

As evidenced by the gel electrophoresis photographs (FIG. 4) shown from experiment 2 regarding exon 8, the collagen-enriched gum substance performed markedly better than the plain chewing gum as a cell adherent. The samples taken via the collagen-enriched gum demonstrated a higher intensity fluorescence in banding patterns.

The four completed experiments established that a collagen-enriched chewing gum has greater potential for collecting oral mucosal cells and exon 8 on the TP53 gene of chromosome 17 as a prospective cell marker for mutations that may predispose individuals to oral squamous cell carcinoma (OSCC). Evidence was found indicating that this screening method could apply to those with genetic predispositions or those exposed to environmental factors such as smoking or chewing tobacco, as the individuals involved in this study with such influences regularly demonstrated a lack of amplification indicating genetic alterations within this gene locus.

Referring now to FIG. 5, the gel electrophoresis results of Experiment No. 2 are shown as an example of how a determination of primer set efficiency was accomplished. Primer sets were chosen from exons 5, 7 and 8 of the TP53 gene. All primers were 19 to 21 bases in length. The purpose of this experiment was to determine which primer set was more differential and would amplify the gum samples. Selection was based on production of an amplicon and the intensity of fluorescence from an ethidium bromide-stained agarose gel at 365 nm.

The polymerase chain reaction was performed in a Biometra TProfessional thermal cycler at the following parameters:

| | |
|---|---|
| 95° C. | 5 minutes |
| 35 cycles | 95° C. 2 minutes |
| | 55° C. 30 seconds |
| | 72° C. 30 seconds |
| 72° C. | 5 minutes |
| 4° C. | Hold |

The gel was photographed with an iPhone using a Major Science UV transilluminator at 365 nanometers. Primer sets used for the TP53 gene all shown in the 5' to 3' direction include:

Exon 5 forward (SEQ ID NO: 1):
TTT CAA CTC TGT CTC CTT CCT
Exon 5 reverse (SEQ ID NO: 2):
GCC CCA GCT GCT CAC CAT C
Exon 7 forward (SEQ ID NO: 3):
GTG TTG TCT CCT AGG TTG GC
Exon 7 reverse (SEQ ID NO: 4):
TGT GCA GGG TGG CAA GTG GC
Exon 8 forward (SEQ ID NO: 5):
CCT ATC CTG AGT AGT GGT AA
Exon 8 reverse (SEQ ID NO: 6):
TCC TGC TTG CTT ACC TCG CTT As shown in FIG. 5, the arrows point to just under 200 base pairs (100 bp-base pair ladder) that represents the position of the expected amplicon. The different lanes as illustrated show the primers as primer 5 from exon 5 of the TP53 gene (lanes 4-13), primer 7 from exon 7 of the TP53 gene (lanes 16-25), and primer 8 from exon 8 of the TP53 gene (lanes 28-35). The production of the produced amplicon and differential sample amplification indicates the advantageous screening for genomic sequence variations and mutations located on exon 8 of the TP53 gene located on chromosome 17.

Tests were also performed to determine the efficiency of primer 8 at detecting mutations within the priming sites of exon 8 in the TP53 gene and determine if 40 cycles was needed for amplification. The electrophoresis gel results are shown in FIG. 6. This PCR was run for 40 cycles rather than the 35 cycles used in Experiment No. 2. The amplicons seen in the reactions of the past smoker and oral cancer patient are not as intense as that seen in the non-smokers. However, slight amplification may suggest that 40 cycles would not be appropriate for screening. Exon 8 appears to be the best choice for preliminary screening of oral squamous cell carcinomas. It was determined that using exon 8 at 35 cycles may be better diagnostically for screening. This suggests that patients with squamous cell oral cancer may be screened with chewing gum and that using collagen as an additive results in a better fluorescent signal from the PCR amplification. Oral cancer patients and past smokers may have a mutation in exon 8 of the TP53 gene that prevents either the forward or reverse primer from annealing to this site, resulting in loss of amplification.

As shown in FIG. 6, the arrow indicates the expected amplicon location of slightly less than 200 base pairs (bp). Lanes 1 and 13 correspond to the 100 bp ladder from New England Biolabs similar to a control and lane 12 was a negative control with only water. Lanes 2-11 are for specific individuals as identified in FIG. 6 with lanes 2 and 6 representing the same individual as a non-smoker and the gum with no additive as the molecular adherent such as collagen. As indicated, kaolin was also tested as an additive with the results not as good as the additive collagen.

In accordance with a non-limiting example, the disclosed method collects oral mucosal or epithelial cells from a patient and evaluates pre-cancerous or cancerous lesions for oral cancer in the patient. The patient or subject may be given a polymeric gum or resin coated in a collagen or other matrix material, and chew the gum for a minimum amount of time, e.g., for about 5 minutes up to about 30 minutes, after which the gum is deposited in a collection tube containing a solution that maintains eukaryotic mammalian cellular integrity. The gum in this example may be shipped to a microbial or molecular lab that performs the polymerase chain reaction using oligonucleotide primers that are specific for genetic mutations seen in the most common types of oral cancers as described above. The time frame needed to incorporate adequate epithelial or mucosal cells into the gum-base may be a minimum of five minutes up to 30 minutes. The gum may be manipulated by the tongue to several positions within the oral cavity including the vestibules of the cheek, the soft palate, underneath the tongue, and the hard palate. There should be no eating, drinking, or chewing (gum, tobacco, etc.) for at least 30 minutes before the test.

In an example, it is possible to form cellular debris and resuspend cellular DNA trapped in the gum or resin by physically chopping the gum, exposing the gum to sound waves to dislodge cells in a sonication process, vortexing, or exposing the gum to a type of electromagnetic radiation, either infrared or ultraviolet. The cellular debris may be used as a template source in a polymerase chain reaction (PCR) in this example of DNA amplification. The oligonucleotide primers may be chosen based on the genomic sequence variations seen in genes that are indicative of oral cancer mutations or sequences as described above. The amplified DNA may be visualized through labeled DNA based on fluorescent labeling, radioactive labeling, or another form of labeling an amplicon, such as a tagged primer. The DNA sequences may be analyzed in real time (RT-PCR), or by agarose gel using a chemical such as ethidium bromide that intercalates into DNA bases. The process may include loop-mediated isothermal amplification (LAMP) single-tube example as a form of amplification, which can be performed without additional equipment and at room temperature. Thus, the DNA identification may be visualized, making a possible "in office" test kit.

A column may be used to collect messenger RNA (mRNA) from the sample using reverse transcriptase to produce complementary DNA (cDNA), then using fluorometrically labeled oligonucleotides to enumerate expression levels of pre-cancerous or cancerous genetic mutations. An example is digital drop PCR. An example column may be a spin column-based nucleic acid purification. Reverse transcription loop-mediated isothermal amplification may combine LAMP with a reverse transcription to detect RNA.

It is possible to incorporate a sodium dodecyl sulfate-polyacrylamide (SDS-PAGE) gel that may be used to separate cellular proteins from the collected sample. The gel may be transferred to a solid-phase material, followed by Western blotting using either radioactively, fluorometric or similar techniques. Monoclonal antibodies may be labeled to determine the presence of a protein that indicates a pre-cancerous or cancerous mutation in a gene indicative of oral cancer.

The polymeric gum may be a resin or chewing gum formed from different synthetic or natural elastomers. Examples include natural rubber, such as smoked or liquid latex and guayule, and natural gums, such as jelutong, lechi caspi, perillo, sorva, massaranduba balata, massaranduba chocolate, nispero, rosindinha, chicle, gutta hang kang, and their combinations. Synthetic elastomer and natural elastomer concentrations may vary depending on whether the gum in which the base is used is adhesive or conventional, bubble gum or regular gum. Different natural elastomers include jelutong, chicle, sorva and massaranduba balata. Elastomer plasticizers may include natural rosin esters, including glycerol esters or partially hydrogenated rosin, glycerol esters of polymerized rosin, glycerol esters of partially dimerized rosin, glycerol esters of rosin, pentaerythritol esters of partially hydrogenated rosin, methyl and partially hydrogenated methyl esters of rosin, pentaerythritol esters of rosin; synthetics such as terpene resins derived from alpha-pinene, beta-pinene, and/or d-limonene; and any suitable combinations of the foregoing. The preferred elastomer plasticizers may vary depending on the specific application, and on the type of elastomer which is used.

It is possible to use different techniques for purification and lyse the chewing gum and yield product from tray samples. Samples may be eluted in a buffer or water may be ready for use in amplification reactions or for further storage. Purified DNA may include proteins, nucleases and other inhibitors. It is possible to use spin columns for purification of high-quality DNA with flexible elution volumes. If lysing is used, it may occur under denaturing conditions.

In an example, the addition of abrasives commonly seen in toothpaste at low concentrations may be incorporated and allow for increased mechanical abrasion of the intraoral cavity. These could include: kaolin clay, silica gels, hydrated aluminum oxides, magnesium carbonate, phosphate salts, silicates, calcium pyrophosphate, calcium carbonate, sodium metaphosphate, zirconium silicate, mica (water ground 325 mesh as an example), sodium bicarbonate, dibasic calcium phosphate dihydrate, aluminum hydroxide gel, or the incorporation of pressurized carbon dioxide. The addition of proteins that are known to have an affinity and adhesion to epithelial cells may assist in a higher level of cell incorporation into the gum. This may limit the time frame for chewing since these proteins could be lost as the chewing time increases. The proteins include the following examples: collagen type I and IV, albumen, and fibronectin, which are additives and supplements currently used in either gum or supplements.

The experiments described above show the advantageous use of collagen. The gum may be coated with different types of collagen or other matrix. Collagen may have different helices that may provide structure and support to the gum and with the helices, bind or contain greater amounts of protein and DNA.

The collagen and protein and DNA may spontaneously form self-assembling complex systems in aqueous solutions, such as induced by electrostatic interactions between neutral collagen cylinders having a strong dipole moment and negatively charged DNA cylinders with a final complex formed by hydrogen bonds between different donor groups of collagen and phosphate acceptor groups of DNA. Thus, collagen may attract and hold greater amounts of DNA during the chewing process. The collagen is preferably added to the gum during formation or it may be coated in other examples.

If the process uses a spin column-based nucleic acid purification, the nucleic acid may bind to the solid phase of silica and the different oral epithelial cells may be lysed so that the cell membranes break to free the nucleic acid. A buffer solution may be added to the sample, such as with ethanol or isopropanol, to form a binding solution that is transferred to a spin column and placed into a centrifuge that forces the binding solution through the silica gel membrane that is inside the spin column. Under optimum pH and salt concentration when the binding solution is optimal, the nucleic acid binds to the silica gel membrane as a solution passes through. The flow through is removed and a wash buffer added to the spin column, which is again centrifuged. The wash buffer is decanted off and the DNA is eluted with an elution buffer through the column. The nucleic acid may be collected from the bottom of the column.

As noted before, the SDS-PAGE system may be used to separate proteins on the basis of differences in their molecular weight, such as between 5 and 250 kilodaltons (kDa). Different blotting techniques may be used.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that the modifications and embodiments are intended to be included within the scope of the dependent claims.

---

---

The invention claimed is:

1. A method of screening a patient for invasive squamous cell carcinoma, comprising:

collecting a sample of chewing gum from a patient that had chewed the chewing gum for a minimum of 5 minutes up to 30 minutes, wherein the chewing gum includes 1% to about 4% added collagen;

placing a sample of the chewed chewing gum into a microcentrifuge tube of only sterile saline to form a saline solution gum mixture within the microcentrifuge tube;

vortexing the microcentrifuge tube of saline solution gum mixture to form a template saline solution within the microcentrifuge tube;

performing a polymerase chain reaction (PCR) on a sample of the template saline solution from the microcentrifuge tube using an oligonucleotide primer set comprising the nucleotide sequences of SEQ ID NO:5 and SEQ ID NO:6 to amplify nucleic acids from exon 8 of the TP53 gene;

following amplification, loading a sample of the amplified nucleic acids obtained from the PCR into an agarose electrophoresis gel containing an ethidium bromide solution, and running the electrophoresis gel to obtain bands of DNA fragments;

after running the agarose electrophoresis gel, transilluminating the photographing the bands at about 365 nanometers; and screening the patient as having a predisposition to invasive squamous cell carcinoma when an amplicon occurs at just under 200 base pairs indicative of a mutation in exon 8 of the TP53 gene that had prevented either the forward or reverse primer from annealing to this site, resulting in loss of amplification, wherein the method does not comprise cell lysing followed by a DNA extraction step.

2. The method of claim 1 wherein the chewing gum includes Polyhydroxyalkanotate or a copolymer thereof.

3. The method of claim 1 wherein an oligonucleotide primer sequence for a forward primer comprises the nucleotide sequence of SEQ ID NO:5: CCT ATC CTG AGT AGT GGT AA, and an oligonucleotide primer sequence for a reverse primer comprises the nucleotide sequence of SEQ ID NO:6: TCC TGC TTG CTT ACC TCG CTT.

4. The method of claim 3 wherein an amplicon length for the DNA template is about 165 base pairs.

5. The method of claim 1 comprising loading the sample of the amplified nucleic acids obtained from the PCR into an agarose electrophoresis gel containing the ethidium bromide solution in a Tris-Acetate buffer and running the gel for about 75 minutes at about 80 volts.

* * * * *